United States Patent [19]

Goldfarb

[11] Patent Number: 5,111,814
[45] Date of Patent: May 12, 1992

[54] LARYNGEAL PACEMAKER

[75] Inventor: David Goldfarb, Cherry Hill, N.J.

[73] Assignee: Thomas Jefferson University, Philadelphia, Pa.

[21] Appl. No.: 549,275

[22] Filed: Jul. 6, 1990

[51] Int. Cl.⁵ .............................................. A61N 1/18
[52] U.S. Cl. .................. 128/419 R; 128/733; 128/642; 128/902
[58] Field of Search ............... 128/642, 733, 902, 905, 128/419 R

[56] References Cited

U.S. PATENT DOCUMENTS 4,198,542  4/1980  Ducommun ...................... 179/1 AL
4,685,448  8/1987  Shames et al. ...................... 128/1 R
4,830,008  5/1989  Meer.

OTHER PUBLICATIONS

Document entitled "Laryngeal Pacing in Unilateral Vocal Cord Paralysis", K. Hissayoshi, M.D.; O. Koichi, M.D. et al;., Arch Otolaryngol Head Neck Surg., vol. 116, Jan. 1990.

Primary Examiner—William E. Kamm
Assistant Examiner—Scott M. Getzow
Attorney, Agent, or Firm—Woodcock, Washburn, Kurtz, Mackiewicz & Norris

[57] ABSTRACT

A laryngeal pacemaker stimulates a paralyzed muscle in mirror image synchronism with a normally functioning muscle.

37 Claims, 1 Drawing Sheet

LARYNGEAL PACEMAKER

FIELD OF THE INVENTION

The present invention relates to the area of laryngeal pacemakers.

BACKGROUND OF THE INVENTION

Vocal cord paralysis is a symptom of a disease with many different etiologies. Lesions involving the cerebral cortex, nucleus ambiguous, nodose ganglion, vagus nerve, recurrent laryngeal nerves or superior laryngeal nerves may lead to vocal cord paralysis and resulting incompetency of the larynx. These lesions can be found anywhere from the head, neck, mediastinum or thorax. Structures often involved include the aorta, right subclavian artery, left atrium, esophagus, trachea, thyroid gland, lymph nodes in the neck, mediastinum and lung. Other causes consist of thyroid surgery, cardiovascular surgery, anterior surgical approaches to the cervical vertebra, laryngeal trauma, neoplasms of the thyroid, lung or vagus nerve, inflammatory diseases, antimetabolites, hydrocephalus, meningomyelocele and idiopathic.

Patients with vocal cord paralysis often have problems with airway maintenance and may present with airway obstruction, difficulties protecting the airway during swallowing leading to aspiration, difficulties with speech such a severe hoarseness, poor cough reflex and problems with effort closure of the larynx needed for the valsalva maneuver.

The first rule of treatment is to treat the underlying disease which is causing the vocal cord paralyses. The second rule is that sometimes no treatment is needed. For example, a patient with a recurrent laryngeal nerve paralysis, who has vocal cords in the midline and has an adequate voice and is asymptomatic does not require treatment. Some patients do well with speech therapy, however some require surgery. Surgical procedures consist of nerve repair, nerve muscle pedicles, arytenoidectomy, arytenoidpexy, cricothyroid arthrodesis and teflon injection. These procedures have had limited success. Presently, the surgical procedure of choice for unilateral vocal cord paralysis consists of teflon injection. This procedure leads to pushing the paralyzed vocal cord closer to the midline to meet the opposite normal vocal cord. Although this procedure works well in some patients others still have problems with aspiration and speech. These patients often require a second procedure called a cricopharyngeal myotomy to help prevent aspiration. Nerve repairs and muscle pedicles take many weeks to months, if they work at all. Patients with both sides of the vocal cords paralyzed often have a usable voice but have an inadequate airway. These patients often require tracheotomy, removal of part or all of the arytenoid or part of a vocal cord. These procedures do not restore the larynx to its pre-paralyzed state. There is therefore a need for a device which can restore the normal functions and integrity of the larynx.

Responding to this long felt need, a number of sources in the prior art have suggested electrical stimulation of the larynx based upon physiological parameters. For example, pacemakers have been suggested based on temperature sensors in the airway (Kwang et. al., "Laryngeal Pacemaker Using A Temperature Sensor In The Canine", Laryngoscope, vol. 97, October 1987, pp. 1207-1210) and other parts of respiration (Bergman et. al., "Long Term Implantation Of A System Of Electrical Stimulation Of Paralyzed Laryngeal Musculature In Dogs", Laryngoscope, vol. 98, April 1988, pp. 455-459; Otto et. al., "Coordinated Electrical Pacing of Vocal Cord Abductors In Recurrent Laryngeal Nerve Paralysis", Otolaryngology Head and Neck Surgery, vol. 93, October 1985, pp. 634-638). Stimulating the paralyzed laryngeal musculature based on these parameters, however, does not replicate the natural functioning of this musculature.

SUMMARY OF THE INVENTION

A laryngeal pacemaker according to the invention comprises a sensing electrode for electrical coupling to a first, normally functioning crico-arytenoid muscle for providing electrical signals indicative of muscle activity thereof. The pacemaker also comprises a stimulating electrode for electrical coupling to a second, dysfunctional crico-arytenoid muscle. A processing means is coupled to receive the electrical signals provided by the sensing electrode for the purpose of providing stimulating signals to the stimulating electrode in substantial synchronism with the electrical signals provided by the sensing electrode. Thus, in pacemaker operation, the dysfunctional crico-arytenoid muscle is stimulated in substantial mirror image synchronism with activity of the normal functioning crico-arytenoid muscle. Conveniently, the disclosed pacemaker is implantable.

DETAILED DESCRIPTION OF THE PREFERRED EMBODIMENT

The present invention overcomes limitations in the prior art by sensing the electrical activity (EMG) of a normally functioning muscle contraction in the larynx and stimulating the synchronous contraction of a dysfunctional muscle of the larynx. The result is that the activity of the dysfunctional side of the larynx reflects a mirror image of the activity of the normally functioning musculature of the opposite side. The mirror image synchronous contraction restores the normal functions and integrity of the larynx.

The lateral cricoarytenoid muscle originates in the upper border of the side of the cricoid cartilage, passes obliquely upward and backward, and is inserted into the muscular process of the arytenoid cartilage. When the lateral cricoarytenoid muscles are functioning normally, they close the glottis by rotating the arytenoid cartilages inward so as to approximate the vocal process. When the right or left lateral cricoarytenoid is dysfunctional, speech is impaired due to the loss of the synchronous contraction of these muscles necessary for normal phonation. In the preferred embodiment, an implantable microprocessor-controlled electrical pacemaker is used to stimulate the dysfunctional lateral cricoarytenoid musculature based on the contraction of the normally functioning lateral cricoarytenoid musculature, but a custom, implantable LSI circuit (of a type to be described) may also be employed. The present invention overcomes limitations in the prior art by mimicking the natural mirror image synchronous contraction of the lateral cricoarytenoid muscles and thereby improving phonation.

For this example, it will be assumed that the left lateral cricoarytenoid musculature functions normally and that the right lateral cricoarytenoid musculature is dysfunctional. Thus as used herein, and in the appended claims, the term "normally functioning muscle" means a muscle that receives nerve innervation and is responsive thereto, and the term "dysfunctional muscle" means a muscle that either does not receive nerve innervation (e.g. due to nerve damage or paralysis), or for some reason is not otherwise fully stimulated by the nerve.

Figure 1:
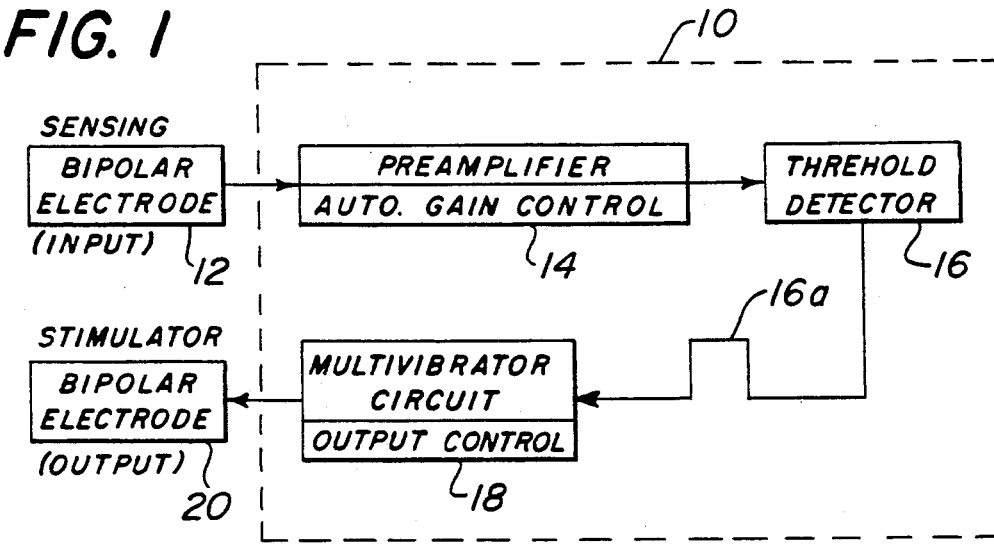
FIG. 1 is a block diagram illustrating a laryngeal pacemaker according to the present invention.

FIG. 1 is a block diagram of one embodiment of an apparatus forming the subject matter of this invention. In this embodiment, the dysfunctional right lateral cricoarytenoid musculature 26 will be stimulated based on the electrical muscle activity of the normally functioning left cricoarytenoid 28.

Figure 2A:
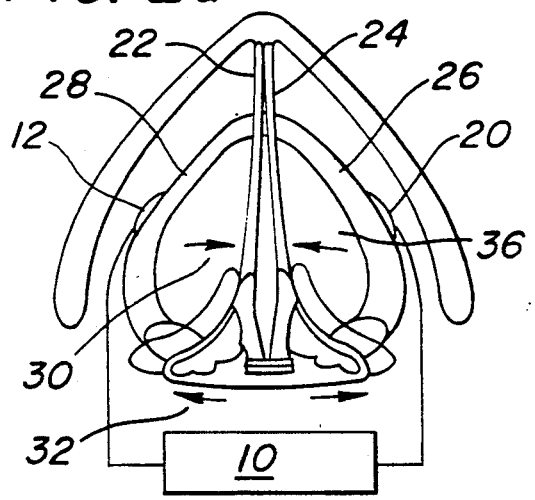
FIGS. 2a and 2b illustrate one view of a human larynx, as well as placement of an electrode on the crico-arytenoid muscles of the larynx according to one embodiment of the invention.

Referring to FIGS. 1 and 2a, an implanted bipolar sensing electrode 12, preferably made of gold or platinum, is placed in contact with the normally functioning left lateral cricoarytenoid musculature 28 of the larynx and connected to the input terminal of the pacemaker 10. The pacemaker 10 comprises an amplifier 14, a threshold detector 16 and a multivibrator circuit 18 as shown. The electrical activity (EMG) of the left lateral cricoarytenoid muscle 28 is sensed by electrode 12 and amplified by preamplifier 14. As the normally functioning left lateral cricoarytenoid muscle 28 contracts, its electrical activity (both frequency and amplitude) increases. When a predetermined electrical threshold is reached, indicating that the normally functioning muscle 28 is contracting, the threshold detector 16 detects this event and provides a stimulator pulse 16a to the multivibrator circuit 18. The magnitude of the predetermined electrical threshold is determined by observing the contraction of the normally functioning musculature. The multivibrator circuit 18 is responsive to the occurrence of pulse 16a to discharge a biphasic pulsatile D.C. current to an implanted bipolar stimulator electrode 20, preferably made of gold or platinum, which is placed in contact with the parallel dysfunctional muscle fibers of the right lateral cricoarytenoid muscle 26. As used herein and in the appended claims, the term "parallel muscle fibers" means muscle fibers in mirror image to each other. The dysfunctional right lateral cricoarytenoid muscle 26 is thus stimulated in mirror image to the activity of the normally functioning left lateral cricoarytenoid 28. The pulse current is preferably adjustable from 0.5 mA to 5.0 mA and the pulse duration is preferably 1 m-sec. in order to induce the desired muscle contraction.

To implant the pacemaker 10, small holes are made in the thyroid cartilage over the area of the lateral cricoarytenoid muscles 26 and 28. The electrodes 12 and 20 are then placed through the thyroid cartilage and secured in place with an appropriate cement to diminish motion artifact. A television monitor and videorecorder are attached to the endoscopes so that the operative and postoperative assessment of vocal cord motion can be documented. The pacemaker 10 and connector wires are preferably similar to cardiac pacemaker design and may be implanted in the neck or anterior chest wall. Once implanted, the pacemaker 10 is able to be reprogrammed transcutaneously.

The present invention overcomes limitations in the prior art by stimulating the dysfunctional musculature based on the electrical activity (EMG) of the normally functioning parallel musculature. The invention has the advantage of mimicking the natural mirror image synchronous movement of the lateral cricoarytenoid muscles necessary for normal phonation. The arrows 32 in FIG. 2a indicate the action of normally functioning or synchronously stimulated lateral cricoarytenoid muscles 26 and 28. The lateral cricoarytenoid muscles 26 and 28 close the glottis 36 by rotating the arytenoid cartilages inward so as to approximate the vocal process. As a result, the left and right vocal cords 22 and 24 are approximated for phonation as illustrated by arrows 30. Thus selective stimulation of the right dysfunctional lateral cricoarytenoid 26 in a mirror image to the left cricoarytenoid 28 will improve speech in patients with unilateral vocal cord paralysis.

Figure 2B:
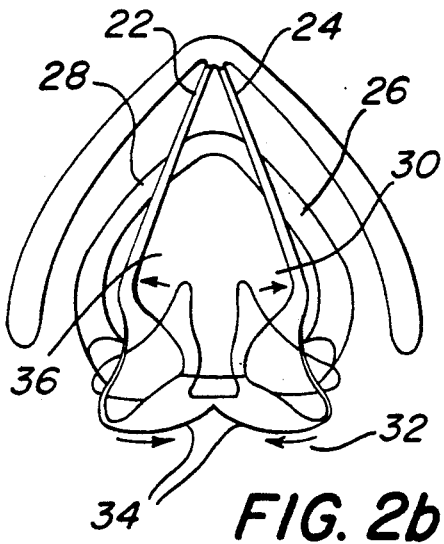

This invention device may also be employed to stimulate muscles which open the glottis 36 and separate the vocal cords 22 and 24 as illustrated in FIG. 2b. An example of one such muscle is the posterior cricoarytenoid 34. Patients with paralysis of both recurrent laryngeal nerves (which innervate the posterior cricoarytenoid musculature) often have severe problems with their airway. These patients frequently need a tracheotomy or part of their vocal cord removed. This invention may be used to stimulate the posterior cricoarytenoid musculature 34 based on the electrical activity of other muscles (not shown) which contract during inspiration and are innervated by other nerves. As illustrated by arrows 32, the posterior cricoarytenoid 34 rotates the arytenoid cartilages outward around a vertical axis passing through the cricoarytenoid joints, so that the vocal processes and the vocal cords attach to them and become widely separated. As a result, the vocal cords 22 and 24 are separated as indicated by arrows 30, consequently opening the glottis 36. Thus the stimulation of the posterior cricoarytenoid 34 results in an opening of the airway as illustrated in FIG. 2b.

Still further, the present invention may be employed to allow dynamic movement and/or to preserve resting motor tone of a reconstructed larynx by stimulating a muscle flap used for laryngeal reconstruction based on the electrical activity of a normally functioning intrinsic muscle of the larynx. A portion of the laryngeal musculature may be removed as a consequence of a laryngectomy or trauma, thus leaving a closing defect. The closing defect is often remedied surgically, by using a muscle flap taken from a neighboring muscle to reconstruct the larynx. The reconstructive muscle flap is preferably a one of the so-called "STRAP" muscles, comprising an omohyoid muscle, a sternohyoid muscle, a thyrohyoid muscle or sternothyroid muscle. The reconstructive muscle flap repairs the closing defect, but is without nervous innervation, and thus is flaccid. The present invention may be used to stimulate the reconstructive muscle flap based on the activity of a normally functioning intrinsic muscle of the larynx, preferably a lateral or posterior cricoarytenoid.

For example, assume that a STRAP muscle flap has been used to reconstruct a closing defect in the left (L) or right (R) side of the larynx post hemi-laryngectomy or trauma. Assume also that the intrinsic laryngeal musculature on the L or R side of the larynx is normally functioning. The electrical activity of the cricoarytenoid musculature, being a normally functioning intrinsic muscle of the larynx, may be employed to stimulate the STRAP muscle used in the reconstructive surgery.

Figure 3:
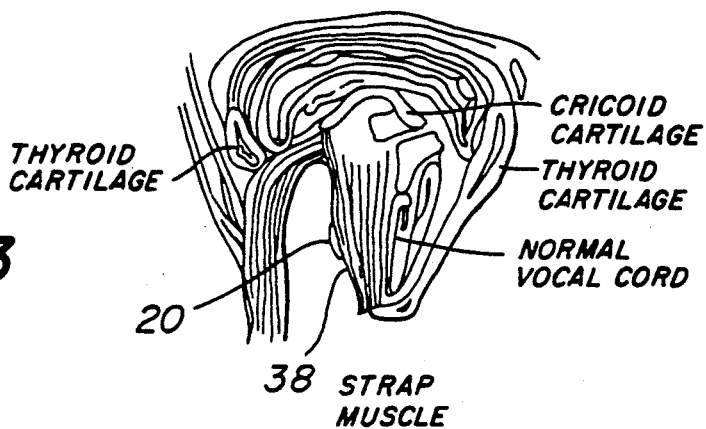
FIG. 3 illustrates another view of the human larynx, and placement of an electrode on a STRAP muscle according to another embodiment of the invention.

Referring to FIGS. 1, 2a and 3, an implanted bipolar sensing electrode 12, preferably made of gold or platinum, is placed in contact with the normally functioning cricoarytenoid musculature 28 of the larynx, and connected to the input terminal of the pacemaker 10. The electrical activity of the normally functioning cricoarytenoid muscle 28 is sensed by electrode 12 and amplified by a preamplifier 14. The threshold detector 16 detects the electrical activity of the normally functioning cricoarytenoid 28. When a predetermined electrical threshold is reached, indicating that the normally functioning muscle 28 is contracting, the threshold detector 16 detects this event and provides a stimulator pulse 16a to the multivibrator circuit 18. The multivibrator circuit 18 is responsive to the occurrence of pulse 16a to discharge a biphasic pulsatile D.C. current to an implanted bipolar stimulator electrode 20, preferably made of gold or platinum, which is placed in contact with the STRAP muscle flap 38. The STRAP muscle flap 38 is stimulated to contract synchronously with the detection of the contraction of the normally functioning cricoarytenoid 28. This has the advantage of allowing dynamic movement of a reconstructed larynx.

The threshold detector 16 also detects the electrical activity of a resting normally functioning muscle and provides a stimulator pulse 16a to the multivibrator circuit 18. The multivibrator circuit 18 is responsive to the occurrence of pulse 16a to discharge a biphasic pulsatile D.C. current to the implanted bipolar stimulator electrode 20, which is placed in contact with the STRAP muscle flap 38. The STRAP muscle flap 38 is stimulated to preserve resting motor tone based on the electrical activity of the normally functioning cricoarytenoid 28. This has the advantage of preserving a resting motor tone of the muscle flap used for laryngeal reconstruction.

The present invention may also be used in many other applications in which it is appropriate for dysfunctional musculature to be stimulated based on the activity of normally functioning musculature. For example, it may be used to stimulate dysfunctional extraocular muscles, based on the contraction of the normally functioning musculature of the opposite eye. Treatment in this manner may stop the double vision which these patients experience.

The present invention may be embodied in other specific forms without departing from the spirit or essential attributes thereof. Accordingly, reference should be made to the appended claims, rather than the foregoing specification, indicating the scope of the invention.

I claim:

1. A laryngeal pacemaker comprising:
    a) a sensing electrode having adapted for electrical coupling to a first, normally functioning crico-arytenoid muscle and for providing electrical signals indicative of muscle activity thereof;
    b) a stimulating electrode having means for electrical coupling to a second, dysfunctional crico-arytenoid muscle;
    c) processing means coupled to receive the electrical signals provided by the sensing electrode for providing stimulating signals to the stimulating electrode in substantial synchronism with the electrical signals provided by the sensing electrode;
    the dysfunctional crico-arytenoid muscle, in pacemaker operation, being stimulated in substantial mirror image synchronism with the activity of the normally functioning crico-arytenoid muscle.

2. Pacemaker according to claim 1 wherein the processing means is implantable.

3. Pacemaker according to claim 1 wherein the electrodes are bipolar.

4. Pacemaker according to claim 1 wherein the processing means comprises:
    a) first means for providing an indication that the electrical signal provided on the sensing electrode has reached a predetermined level; and
    b) second means operatively coupled to and responsive to the first means for generating the stimulating signals.

5. Pacemaker according to claim 4 wherein the stimulating signals are biphase D.C. current pulses.

6. Pacemaker according to claim 5 wherein the current pulses have a duration of about 1 msec and a magnitude in the range of about 0.5 mA to 5.0 mA.

7. Laryngeal pacemaker comprising:
    a) an implantable bipolar sensing electrode having adapted for electrical coupling to a first, normally functioning lateral crico-arytenoid muscle for providing electrical signals indicative of muscle activity thereof;
    b) an implantable bipolar stimulating electrode having means for electrical coupling to a second, dysfunctional lateral crico-arytenoid muscle;
    c) implanatable circuit means for coupling to the electrodes for providing indications that electrical signals provided on the sensing electrode have reached a predetermined level and for generating stimulating signals in response thereto, the implantable circuit means providing the stimulating signals in substantial synchronism with the electrical signals provided by the sensing electrode, the dysfunctional lateral crico-arytenoid muscle, in pacemaker operation, being stimulated in substantial mirror image synchronism with the activity of the normally functioning lateral crico-arytenoid muscle.

8. Pacemaker according to claim 7 wherein the stimulating signals are biphase D.C. current pulses.

9. Pacemaker according to claim 8 wherein the current pulses have a duration of about 1 msec and a magnitude in the range of about 0.5 mA to 5.0 mA.

10. Laryngeal pacing method comprising the steps of:
    a) sensing electrical activity of a normally functioning one of a pair of crico-arytenoid muscles;
    b) artificially stimulating a dysfunctional one of the pair of crico-arytenoid muscles in substantial mirror image synchronism with the sensed electrical activity.

11. A laryngeal pacemaker comprising:
    a) a sensing electrode having adapted for electrical coupling to a normally functioning muscle which contracts during inspiration and for providing electrical signals indicative of muscle activity thereof;
    b) a stimulating electrode having means for electrical coupling to a dysfunctional posterior crico-arytenoid muscle;
    c) processing means coupled to receive the electrical signals provided by the sensing electrode for providing stimulating signals to the stimulating electrode in substantial synchronism with the electrical signals provided by the sensing electrode;
    the dysfunctional posterior crico-arytenoid muscle, in pacemaker operation, being stimulated in substantial synchronism with the activity of the normally functioning muscle.

12. Pacemaker according to claim 11 wherein the processing means is implantable.

13. Pacemaker according to claim 11 wherein the electrodes are bipolar.

14. Pacemaker according to claim 11 wherein the processing means comprises:
   a) first means for providing an indication that the electrical signal provided on the sensing electrode has reached a predetermined level; and
   b) second means operatively coupled to and responsive to the first means for generating the stimulating signals.

15. Pacemaker according to claim 14 wherein the stimulating signals are biphasic D.C. current pulses.

16. Pacemaker according to claim 15 wherein the current pulses have a duration of about 1 m-sec. and a magnitude in the range of about 0.5 mA to 5.0 mA.

17. Laryngeal pacemaker comprising:
   a) an implantable bipolar sensing electrode having adapted for electrical coupling to a normally functioning muscle which contracts during inspiration and for providing electrical signals indicative of muscle activity thereof;
   b) an implantable bipolar stimulating electrode having means for electrical coupling to a dysfunctional posterior crico-arytenoid muscle;
   c) implantable circuit means coupled to the electrodes for providing indications that electrical signals provided on the sensing electrode have reached a predetermined level and for generating stimulating signals in response thereto, the implantable circuit means providing the stimulating signals in substantial synchronism with the electrical signals provided by the sensing electrode, the implantable circuit means causing the dysfunctional posterior crico-arytenoid muscle to be stimulated in substantial synchronism with the activity of the normally functioning muscle.

18. Pacemaker according to claim 17 wherein the stimulating signals are biphasic D.C. current pulses.

19. Pacemaker according to claim 18 wherein the current pulses have a duration of about 1 m-sec. and a magnitude in the range of about 0.5 mA to 5.0 mA.

20. Laryngeal pacing method comprising the steps of:
   a) sensing electrical activity of a normally functioning muscle which contracts during inspiration;
   b) artificially stimulating a dysfunctional posterior cricoarytenoid muscle in substantial synchronism with the sensed electrical activity.

21. A laryngeal pacemaker comprising:
   a) a sensing electrode having adapted for electrical coupling to a first, normally functioning cricoarytenoid muscle and for providing electrical signals indicative of muscle activity thereof;
   b) a stimulating electrode having means for electrical coupling to a reconstructive muscle flap;
   c) processing means coupled to receive the electrical signals provided by the sensing electrode for providing stimulating signals to the stimulating electrode in substantial synchronism with the electrical signals provided by the sensing electrode;
   the reconstructive muscle flap, in pacemaker operation, being stimulated in substantial synchronism with the activity of the normally functioning cricoarytenoid muscle.

22. Laryngeal pacemaker according to claim 21 wherein the reconstructive muscle flap is a STRAP muscle.

23. Laryngeal pacemaker according to claim 22 wherein the STRAP muscle is one of a omohyoid, sternohyoid, thyrohyoid or sternothyroid muscle.

24. Laryngeal pacemaker according to claim 21 wherein the processing means is implantable.

25. Laryngeal pacemaker according to claim 21 wherein the electrodes are bipolar.

26. Laryngeal pacemaker according to claim 21 wherein the processing means comprises:
   a) first means for providing an indication that the electrical signal provided on the sensing electrode has reached a predetermined level; and
   b) second means operatively coupled to and responsive to the first means for generating the stimulating signals.

27. Laryngeal pacemaker according to claim 26 wherein the stimulating signals are biphasic D.C. current pulses.

28. Laryngeal pacemaker according to claim 27 wherein the current pulses have a duration of about 1 m-sec. and a magnitude in the range of about 0.5 mA to 5.0 mA.

29. Laryngeal pacing method comprising the steps of:
   a) sensing electrical activity of a normally functioning intrinsic laryngeal muscle;
   b) artificially stimulating a reconstructive muscle flap in substantial synchronism with the sensed electrical activity.

30. Laryngeal pacemaker comprising:
   a) an implantable bipolar sensing electrode having adapted for electrical coupling to a normally functioning intrinsic muscle of the larynx and for providing electrical signals indicative of resting muscle tone thereof;
   b) an implantable bipolar stimulating electrode having means for electrical coupling to a reconstructive muscle flap;
   c) implantable circuit means coupled to the electrodes having means for providing indications that electrical signals provided on the sensing electrode are within a range indicative of resting motor tone and for generating stimulating signals in response thereto, the implantable circuit means providing the stimulating signals in substantial synchronism with the electrical signals provided by the sensing electrode, the implantable circuit means causing the reconstructive muscle flap to be stimulated to maintain the resting motor tone.

31. Laryngeal pacemaker according to claim 30 wherein the reconstructive muscle is a STRAP muscle.

32. Laryngeal pacemaker according to claim 31 wherein the STRAP muscle is one of an omohyoid, a sternohyoid, a thyrohyoid, or a sternothyroid.

33. Laryngeal pacemaker according to claim 30 wherein the normally functioning intrinsic muscle of the larynx is a cricoarytenoid.

34. Laryngeal pacemaker according to claim 30 wherein the processing means comprises:
   a) first means for providing an indication of the level of the electrical signal provided on the sensing electrode; and
   b) second means operatively coupled to and responsive to the first means for generating the stimulating signals.

35. Laryngeal pacemaker according to claim 34 wherein the stimulating signals are biphasic D.C. current pulses.

36. Laryngeal pacemaker according to claim 35 wherein the current pulses have a duration of about 1 m-sec. and a magnitude in the range of about 0.5 mA to 5.0 mA.

37. Laryngeal pacing method comprising the steps of:
a) sensing the level of electrical activity of a resting normally functioning intrinsic laryngeal muscle;
b) artificially stimulating a reconstructive muscle flap continuously to preserve resting motor tone.

* * * * *

UNITED STATES PATENT AND TRADEMARK OFFICE
CERTIFICATE OF CORRECTION

PATENT NO.  : 5,111,814

DATED       : May 12, 1992

INVENTOR(S) : David Goldfarb

It is certified that error appears in the above-identified patent and that said Letters Patent is hereby corrected as shown below:

In the Claims:
Col. 5
Claim 1, line 55, after "having" insert --means--
Col. 6
Claim 7, line 21, after "having" insert --means--
Col. 6
Claim 11, line 55, after "having" insert --means--
Col. 7
Claim 17, line 21, after "having" insert --means--
Col. 7
Claim 21, line 54, after "having" insert --means--
Col. 8
Claim 30, line 33, after "having" insert --means--

Signed and Sealed this

Twenty-ninth Day of June, 1993

Attest:

MICHAEL K. KIRK

Attesting Officer

Acting Commissioner of Patents and Trademarks